United States Patent [19]

Pringiers et al.

[11] 4,383,450

[45] May 17, 1983

[54] METHOD AND APPARATUS FOR DETERMINING STATIC AND DYNAMIC CHARACTERISTICS FROM A VISCOUS-ELASTIC MATERIAL

[75] Inventors: Pierre Pringiers, Stalhille; Clement De Meersman, Moorsel, both of Belgium

[73] Assignee: Bergougnan - Benelux, Belgium

[21] Appl. No.: 210,605

[22] Filed: Nov. 26, 1980

[30] Foreign Application Priority Data

Nov. 30, 1979 [NL] Netherlands ................... 7908675

[51] Int. Cl.³ ............................................. G01N 3/42
[52] U.S. Cl. ......................................... 73/790; 73/81
[58] Field of Search .................. 73/81, 789, 822, 818, 73/12, 788, 790, 811, 82; 364/551

[56] References Cited

U.S. PATENT DOCUMENTS

| | | | |
|---|---|---|---|
| 3,421,364 | 1/1969 | Moneypenny et al. | 73/82 |
| 3,545,261 | 12/1970 | Maleschew et al. | 73/81 |
| 3,699,808 | 10/1972 | Ford et al. | 73/789 X |
| 4,074,569 | 2/1978 | Sambrook et al. | |
| 4,094,188 | 6/1978 | Bellouin et al. | 73/81 |

FOREIGN PATENT DOCUMENTS

| | | |
|---|---|---|
| 6616325 | 6/1967 | Netherlands . |
| 939310 | 10/1963 | United Kingdom . |
| 963502 | 7/1964 | United Kingdom . |
| 1225763 | 3/1971 | United Kingdom . |
| 1425038 | 2/1976 | United Kingdom . |
| 1543945 | 4/1979 | United Kingdom . |

OTHER PUBLICATIONS

Hockett, J. E. et al., Cam Plastometer Data Acquisition System, from Journal of Physics E., vol. 4, Jul. 1971, pp. 520-522.

Primary Examiner—Jerry W. Myracle
Attorney, Agent, or Firm—Scully Scott, Murphy & Presser

[57] ABSTRACT

There is described a measuring method for static and dynamic material characteristics in which to that material the above-defined characteristics of which are to be measured, there is applied by means of a force F, a constant predetermined deformation by compression or pressing-in and the deformation is retained for at least 10 seconds and preferably at least 15 seconds, whereby the building-up of force F from a moment zero which corresponds to that time where the force is applied, and the decrease thereof after said constant deformation has been reached, is measured as a function of the time, and the material characteristics are determined from suitable formulas.

19 Claims, 6 Drawing Figures

METHOD AND APPARATUS FOR DETERMINING STATIC AND DYNAMIC CHARACTERISTICS FROM A VISCOUS-ELASTIC MATERIAL

This invention relates to a method for determining static and dynamic characteristics, more particularly the elasticity modulus $E'$ and the loss modulus $E''$, from a viscous-elastic material, the relaxation modulus $E(t)$ of which fulfills the equation $E(t)=A+Bt^{-\alpha}$ with $E(t)$ being the relaxation modulus, A,B and constants and t the time in seconds, as a function of the frequency the material is subjected to.

By viscous-elastic materials there should be understood here, among others thermosetting rubbers, mixtures of rubber and filling material, plastic materials, thermoplastic rubbers and similar.

The knowledge of the dynamic material characteristics is notably necessary when sizing rubber components by means of digital computer programs for use in supporting machines and buildings, suspending motors and engines, fastening shock absorbers, etc.

With the conventional methods known up to now for determining such material characteristics, use is generally made of heavy and expensive machines with hydraulic and mechanical energizing which have to generate heavy forces.

Material characteristics measured according to such methods are dependent on the size of the test sample being used and on the deformation conditions.

Consequently the result thus obtained does not give a pure material characteristic.

Moreover to obtain the dependence upon the frequency of the material characteristics, theoretical measurings should be made at all frequencies, which is usually impossible.

Finally characteristics measured according to the usual methods cannot be used directly for digital computing methods for other deformation levels.

The invention has mainly for object to obviate the various drawbacks as defined above and to provide a method which allows to determine a pure material characteristic which is independent from the shapes, sizes and applied deformation, and which does moreover give directly the frequency dependence of the material characteristics.

According to the invention, to that material the above-defined characteristics of which are to be measured, there is applied by means of a force F, a constant predetermined deformation by compression or pressing-in and said deformation is retained for at least 10 seconds and preferably at least 15 seconds, whereby the building-up of force F from a moment zero which corresponds to that time where said force is applied, and the decrease thereof after said constant deformation has been reached, is measured as a function of the time, and said material characteristics are determined on the basis of the following formulas:

$$E(t) = f[f_1(a), F_2(b), F(t)] \quad (I)$$

with
 a = impression depth;
 b = size and shape of the impression body or section of test sample $$E(t) = A + Bt^{-\alpha} \quad (II)$$

$$E^x(\omega) = E'(\omega) + jE''(\omega) \quad (III)$$

with $\omega = 2\pi F$ wherein f is the frequency;

$$E'(\omega) = \frac{\alpha B \omega^\alpha}{2(1+\alpha)} \Gamma\left(1-\frac{\alpha}{2}\right) \Gamma\left(\frac{\alpha}{2}\right) + A \quad (IV)$$

$$E''(\omega) = \frac{\alpha B \omega^\alpha}{2\Gamma(1+\alpha)} \Gamma\frac{(1-\alpha)}{2} \Gamma\frac{(1+\alpha)}{2} \quad (V)$$

wherein $\Gamma$ is the gamma function.

Usefully said deformation is applied to the material in less than 0.5 seconds.

In a particular embodiment of the invention, said deformation is applied by means of a ball-shaped impression body with a diameter which lies preferably between 0.5 and 3 mm, to a depth which is equal at the most to the radius of said body.

The invention further pertains to an apparatus for determining experimentally static and dynamic material characteristics according to the above method.

The apparatus comprises a pressure body which is made fast together with a force transducer to a component which is movable over a constant determined distance, which force transducer measures the force exerted along the component movement direction on said pressure body as a function of the time, whereby detection means are provided to switch on said force transducer at that moment where said movable component is brought from a rest position to an impression position.

In a more particular embodiment of the invention, said component is comprised of a rod which is slidably mounted inside a fixed guide and is provided at that end thereof removed from the impression body, with a stop member which cooperates on the one hand with a resilient member provided between the guide and the stop member, and on the other hand with a cam which is rotatable about a rotation axis which lies substantially at right angle to the rod axis, with an eccentricity which corresponds substantially to half said constant determined movement distance of the rod and thus can bring said rod together with the impression body, from a rest position in the direction of a test sample to an impression position, whereby in said impression position the stop member is pressed by the cam against the guide in such a way that in said position, a rigid dynamic connection is obtained between the rod, the impression body and the apparatus frame, and whereby detection means are provided for switching on said force transducer at that moment where the rod is moved in the direction of the test sample towards said impression position.

Other details and features of the invention will stand out from the following description given by way of non limitative example and with reference to the accompanying drawings, in which:

FIG. 4 is a diagrammatic showing of a vibration system the invention is applied to.

In the various figures the same reference numerals pertain to similar components.

The most important material characteristics which can be determined with the method according to the invention may be defined as follows.

Let us consider that for a periodic deformation of a rubber element with a length $l_o$ to a length $l$, there appears a force F.

Said force F is formed by the two following components:

F' in phase with the deformation $l/l_o$;

F" lagging by 90° in time relative to the deformation $l/l_o$;

$l/l_o$ is called the deformation ($\epsilon$);

$S_O$ is the cross-section of the rubber element before the deformation;

S is the cross-section of the rubber element after the deformation.

Two modulus may be defined from the above:
the elasticity modulus $E' = F'/\epsilon S$ and
the loss modulus $E'' = F''/\epsilon S$.

For measuring said elasticity modulus and loss modulus, the procedure according to the invention is as follows:

That material said characteristics of which are to be determined is subjected to a constant predetermined deformation by compression or impression, which is preferably such that the general change in the deformed material cross-section at right angle to the direction of the applied force F is to be neglected.

Usefully said force F is applied but to a portion from a determined side of the material, for example in the form of a point load, and this in such a way that the general material deformation can be neglected.

Generally the impression depth in the material is at the most 10% from the test sample thickness.

However it may be desirable in some cases to apply stronger deformations. In this case it may be desirable to take into account in the formulas some experimentally-determined corrections which thus consider the kind of the general deformations thus obtained.

This may for example be useful when the applied deformation is obtained substantially over a complete side from the test sample by means of pressure plates.

Furthermore said deformation is retained for at least 10 seconds and preferably 15 seconds and simultaneously the building-up of said force F is measured as a function of the time from a moment zero, which corresponds to that moment where the force is applied, and the force decrease after said constant deformation has been reached.

Figure 1:
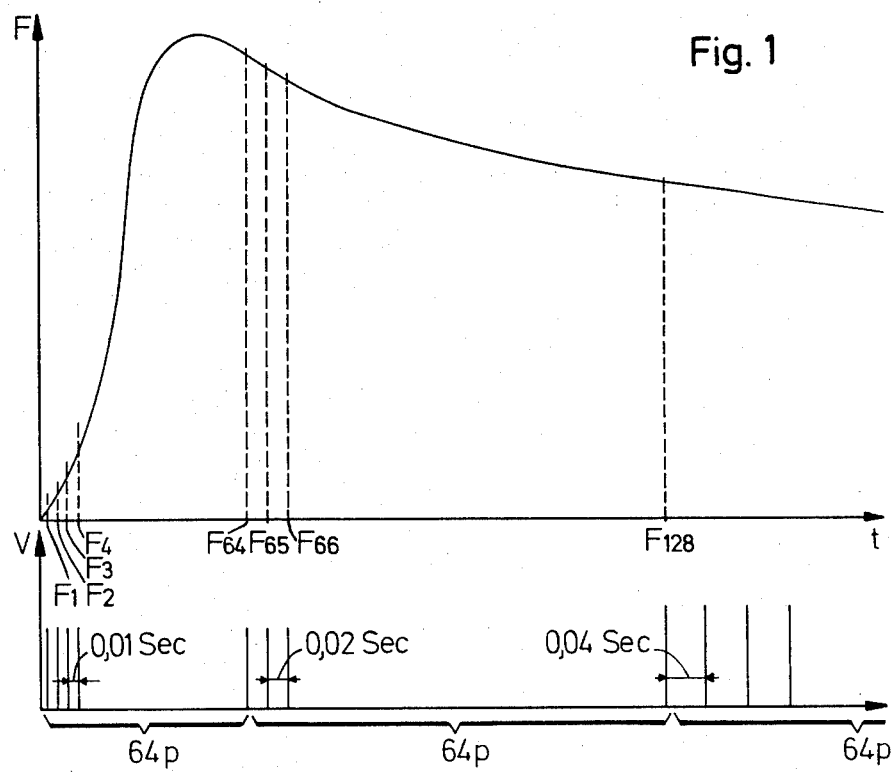
FIG. 1 is a graphic showing of the impression force on the test sample as a function of the time.

According to the invention, it is of very great interest that the measurings of the force build-up from the momemt zero to that moment where the force decreases again, be made very carefully to allow locating as accurately as possible the maximum of the curve according to FIG. 1. It is always observed that this is absolutely necessary for determining the elasticity modulus at high frequencies. It should preferably be insured that the measuring frequency is very high from the moment zero to beyond said maximum, for example in the range from 50 to 200 measurings per second. With the further progress of the force decrease, the measuring frequency can decrease progressively or stepwise.

The data thus measured allow on the basis of the following formulas, to compute both the elasticity modulus and the loss modulus as a function of the frequency the materials are subjected to.

Indeed with the measurings made according to the method, the curve as shown in FIG. 1 is determined and said curve does correspond to the function F(t) from the equation (I) and as a and b are given parameters, E(t) can thus be determined in said equation.

By iteration the constants A, B and $\alpha$ from equation (II) are then determined.

Thereafter on the basis of formulas (IV) and (V) while taking into account the values obtained for A, B and $\alpha$, the elasticity modulus and the loss modulus can be computed as a function of the frequency, which thus gives $E^x$ by making use of formula (III).

To minimize the influence of the force build-up on the computing, said deformation is preferably applied to the material in less than 0.5 seconds and even less than 0.1 seconds.

It is also preferred to use a ball-shaped impression body to apply said deformation, preferably with a diameter lying between 0.5 and 3 mm. The impression depth in the test sample is then equal at the most to the radius of said ball-shaped body.

The test sample can have any shape but does preferably fulfill the following requirements:

the top and bottom sides of the sample are flat and in parallel relationship with one another;

the ratio of the sample thickness to the impression body diameter is at least equal to 5;

the ratio of the shortest spacing from the sample edge to the impression body, to the impression body diameter is at least equal to 4.

The measuring method according to the invention has been intensively tested for ball-shaped impression bodies having diameters falling within the above-defined limits and on rubbers having the following modulus:

$12 N/mm2 > E' > 0,2 N/mm2$ $5 N/mm2 > E'' > 0,1 N/mm2$

As it appears from the above calculations, the method according to the invention can be applied as a rule to every viscous-elastic material, more particularly vulcanized materials the relaxation modulus E(t) of which fulfills the equation (II) as long as the applied deformation both in the impression body and in the material to be tested, remains elastic. The deformation is not necessarily to be applied with a ball but can also occur by means of a cylinder for example; said deformation can also occur due to a small compression of the sample.

Thermo-setting rubbers or rubber mixtures on the basis both of natural rubber and synthetic rubber, for example styrene-butadiene rubbers, polychloroprene, nitrile, ethylenepropylene, butyl, thermo-plastic rubbers, conventional plastic materials such as for example polyethylene, polypropylene, polyurethane, ABS, polyester, epoxy resins, etc. are to be considered therefor.

It is generally to be found that by adapting the method according to the invention, the above-defined characteristics can be measured for any material the elasticity modulus of which lies between 1000 N/mm² and 0.2 N/mm².

Figure 2:
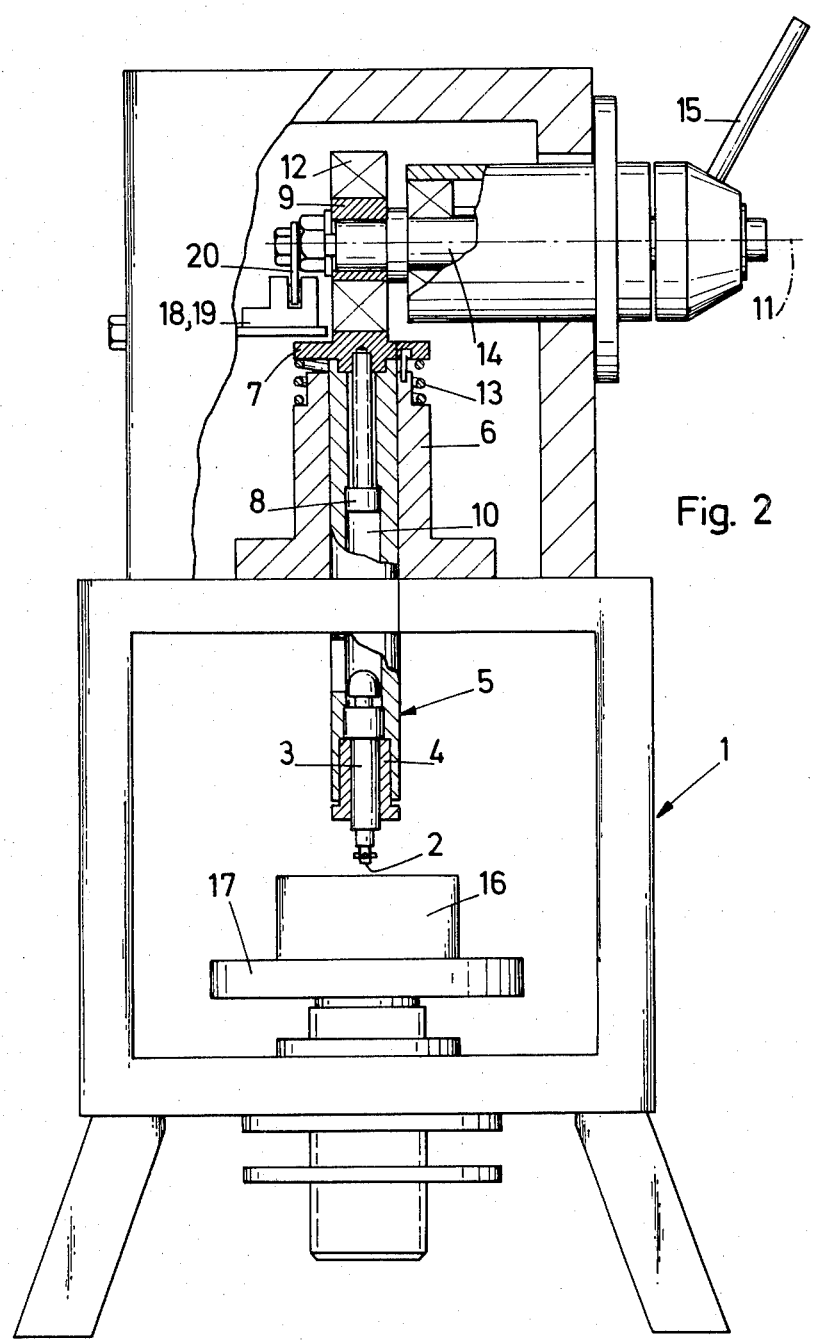
FIG. 2 is a diagrammatic showing in a vertical section, of a particular embodiment of the apparatus according to the invention.

In FIG. 2 is shown a particular embodiment of an apparatus according to the invention for applying the above-defined method. Said apparatus is comprised of a frame 1 which is dynamically very rigid, with a natural frequency higher than 2000 Hertz, in such a way that self-vibrations of said frame have no influence on the measuring.

The apparatus is further provided with a ball-shaped impression body with a diameter lying between 0.5 and 3 mm which bears reference numeral 2 and is screwed fast into an electric force transducer 3 which is surrounded by an isolation 4 against temperature variations and electric noise.

Said force transducer 3 is in turn made fast to the free end of a hollow rod 5 which is movable along the axis thereof over a constant predetermined distance.

The displacement distance of rod 5 along the axis thereof is at the most equal to the radius of the ball-shaped impression body 2.

The force transducer 3 is preferably comprised of a piezo-electric element.

The hollow rod 5 is slidably mounted in a fixed tube-like guide 6 and it is provided at that end thereof removed from the impression body 2 with a stop member 7 which is screwed fast by means of a screw-bolt 8, to said rod 5.

Between said stop member 7 and the corresponding end of guide 6, a coil spring 13 is arranged in co-axial relationship with said rod, while a cam 9 which is rotatable about a rotation axis 11 substantially at right angle to the axis 10 of rod 5, acts through a ball-bearing 12 on that side of stop member 7 which is removed from spring 13. The eccentricity of cam 9 or ball-bearing 12 is equal to half said pre-determined movement distance of rod 5.

Said cam 9 is fast to a pivot pin 14 which lies in coaxial relationship with said rotation axis 11 and to which is also made fast a handle 15.

It is thus possible by rotating said handle 15 over an angle of 180°, to move rod 5 and consequently impression body 2, from a rest position in the direction of a test sample 16 which lies underneath impression body 2 on a height-adjustable table 17, to a position whereby said body 2 is pressed into sample 16.

In said impression position, the stop member 7 lies against guide 6 in such a way that spring 13 is made inoperative and a dynamic rigid connection is insured between rod 5, impression body 2 and apparatus frame 1.

The apparatus is further provided with detection means, more particularly two photocells 18 and 19 in front of which moves an interrupter 20 which is fixed relative to cam 9, which allows to cut-in said force transducer 3 at that moment where rod 5 is moved in the direction of test sample 16 to said impression position.

Figure 3:
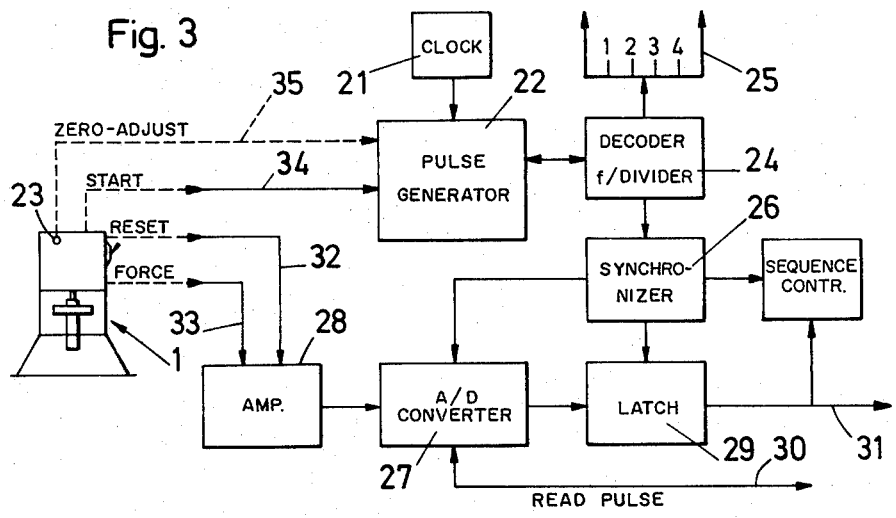
FIG. 3 is a block diagram of the electronic part from the apparatus shown in FIG. 2.

The detection means and force transducer are connected to an electric circuit which has been shown diagrammatically in FIG. 3. Said electronic circuit converts the analog force signal measured by said force transducer, as shown in FIG. 1, into digital form and couples said digital data to the memory of a computer not shown.

The electronic circuit is mainly comprised of a pulse stream generator 22 controlled by a 10 MHz-clock 21, said generator 22 being connected to photocell 18 which allows to give the starting signal. The connection between said photocell and generator is shown by a line 34. Said generator is also connected to a zero-adjust control 33 as shown by a line 35.

The generator 22 is further coupled to a decoding frequency-divider 24.

More particularly said electronic circuit comprises means to cause said converting frequency of the analog force signal into digital form to decrease after a time interval which is longer than the time required to bring said movable component to said impression position. As shown in FIG. 1, during a first time interval for example 64 pulses with a period of 0.1 sec., during a second time interval 64 pulses with a period of 0.02 sec., during a third time interval 64 pulses with a period of 0.04 sec., and finally during a fourth time interval 64 pulses with a period of 0.160 sec., are generated.

Said time intervals have been shown diagrammatically in FIG. 3 in 25.

By means of a synchronizer 26, an instruction is given at each rising pulse flank $F_1$, $F_2$, . . . (see FIG. 1), to an analog-digital converter 27.

The analog force F is coupled from the force transducer 3 through a charge amplifier 28 to the input to said analog-digital converter 27 wherein a conversion to digital signals is made. The connection between the force transducer and charge amplifier 28 is shown by a line 33. Said signals are then stored in a buffer (latch) 29.

Said charge amplifier is further controlled by the second photocell 19, which returns the charge amplifier to the original condition thereof when handle 15 is moved to the impression position. This is shown by the diagrammatic connection 32.

A pulse (flag) is thereafter generated as shown by arrow 30, to let the computer read the digital data from said buffer into the memory, not shown.

Consequently a total of 256 measuring points for force F, distributed over a total measuring time of 16 seconds, are stored in the memory of a computer shown by an arrow 31. The time intervals corresponding to said measuring points are computed from the periods of the clock pulses.

The apparatus thus described with reference to FIG. 2 is used as follows:

A test sample 16 the E' and E" modulus are to be determined and which preferably fulfills the above-defined requirements, is arranged on table 17.

Thereafter said table is so adjusted in the height thereof that the top surface of the test sample, precisely contacts said impression body 2 which lies in rest position, that is in the top position thereof.

The handle 15 is then rotated rapidly, preferably within a time in the range from 0.02 to 0.08 sec., over a 180°-angle to the impression-position, whereby the body 2 enters sample 16 down to a predetermined depth. Due to the shifting of handle 15, two electric pulses are generated in photocells 18 and 19. Said pulses are used to control the pulse stream generator and the charge amplifier from the electronic circuitry, whereby the generated time-varying point loading which is exerted by said impression body 2 on the sample, is directly recorded, as shown graphically in FIG. 1.

Said recorded data then allow determining with the above-defined particular computing method, the E' and E" modulus as well as the relaxation modulus E, in other words the ratio of the time-dependent tension to said constantly-applied impression.

The method according to the invention differs from the generally-known methods for determining the E' and E" modulus due to said modulus being determined directly as a function of the frequency with a single measuring, and this independently from the shape and size of the pertaining viscous-elastic material.

Due to the very accurate determining of the relaxation curve maximum, same is also true for very high frequencies.

With the method according to the invention, a varying force is measured for an applied pre-determined constant deformation. It is then also of very great importance that the apparatus used thereby forms a very rigid unit at the impression time and that preferably a stop is provided at the end of the impression to insure said rigid mechanical connection. This is necessary to prevent vibrations of the impression body relative to the material to be measured.

A practical example of a particular use of the method and apparatus according to the invention is given hereinafter with reference to FIGS. 4 and 5.

Said example does pertain to determining the required elasticity modulus $E'$ and loss modulus $E''$ from four rubber dampers 39 with pre-determined size which are to be used to minimize the transmission of vibrations from an electric motor 36 to the surroundings thereof, more particularly the ground 37. Said motor bears on a concrete mass 38. The revolution frequency of the motor was $f_m = 20$ Hz, while the total weight of the concrete mass and motor was 1 ton. It was required to support sidewise said concrete mass with the rubber dampers 39 having a pre-determined size.

It is requested to lower those dynamic forces which are generated by the motor by a factor 3. With the starting of the motor, the revolution frequency should thus rise from 0 to 20 Hz.

To limit variations of the dynamic force, a damping ratio with a minimum value of 0.1 is specified.

Figure 4:
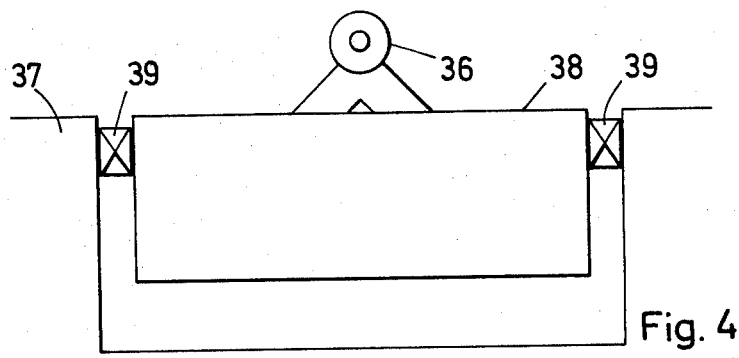
Figure 5:
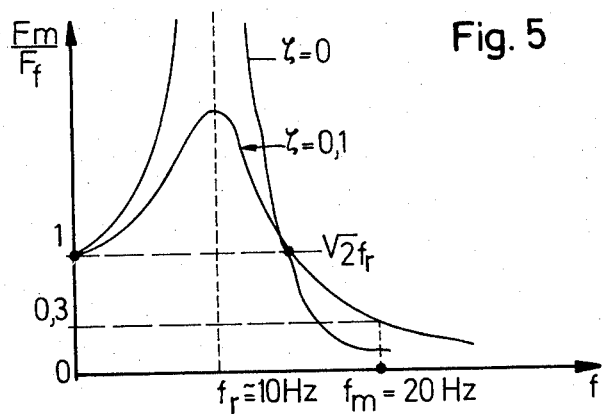
FIG. 5 is a graphic showing of the transfer function from the vibration system as shown in FIG. 4.

The transfer function from the vibration system as shown diagrammatically in FIG. 4, that is the ratio of the dynamic force $F_m$ generated by motor 36 to the dynamic force $F_f$ on the foundation or ground 37 is shown in FIG. 5.

To obtain the above-required reduction factor 3, the own frequency $f_r$ of the motor-mass-damper system lies about 10 Hz.

The given size for the rubber blocks was $200 \times 200 \times 60$ mm.

From these data, the required elasticity modulus $E'$ and loss modulus $E''$ are computed on the basis of the following formulas:

$$f_r = \tfrac{1}{2}\pi\sqrt{\frac{k_d}{m}} \quad \begin{matrix} m = 1000 \text{ kg} \\ f_r = 10 \text{ Hz} \end{matrix}$$

$k_d$ = dynamic rigidity of the rubber blocks at 10 Hz.
$\gamma = 0.1 = C/C_{crit}$
$C$ = damping constant of the rubber elements $$C_{crit} = 2\sqrt{k_d m}$$

$k_d = G'A/h$ and $C \cdot \omega = G''A/h$
$E' = 2(1+V)G'$
$E'' = 2(1+V)G''$
with $G'$ and $G''$ = the corresponding sliding modulus
$\omega = 2\pi f$ (f = frequency)
A = original surface area of the rubber blocks ($200 \times 200$ mm)
h = original height of said rubber blocks (60 mm)

V = 0.5 (Poisson's factor)

By resolving these various equations, the following requirements are obtained which are to be fulfilled by the formulation of the rubber for the blocks 39.

Said requirements may be stated as follows:

$E'(10 \text{ Hz}) = 4.44 \text{ N/mm2}$ $E''(10 \text{ Hz}) \geqq 0.9 \text{ N/mm2}.$ By means of the apparatus as shown in FIG. 2, a series of tests have been made on rubber elements which are prepared according to various formulations. There has been retained thereby a rubber formulation with the following characteristics:

$E' = 4.55 \text{ N/mm2}$ $E'' = 1.1 \text{ N/mm2}.$

From this rubber are then formed blocks with the above-defined size and said blocks are arranged as shown in FIG. 4.

The measured reduction factor was 0.29 which thus corresponds substantially with the requested value.

Such practical results prove that the rubber formulation thus computed and checked with the apparatus according to the invention, fulfills the requirements in the dynamic domain.

Figure 6:
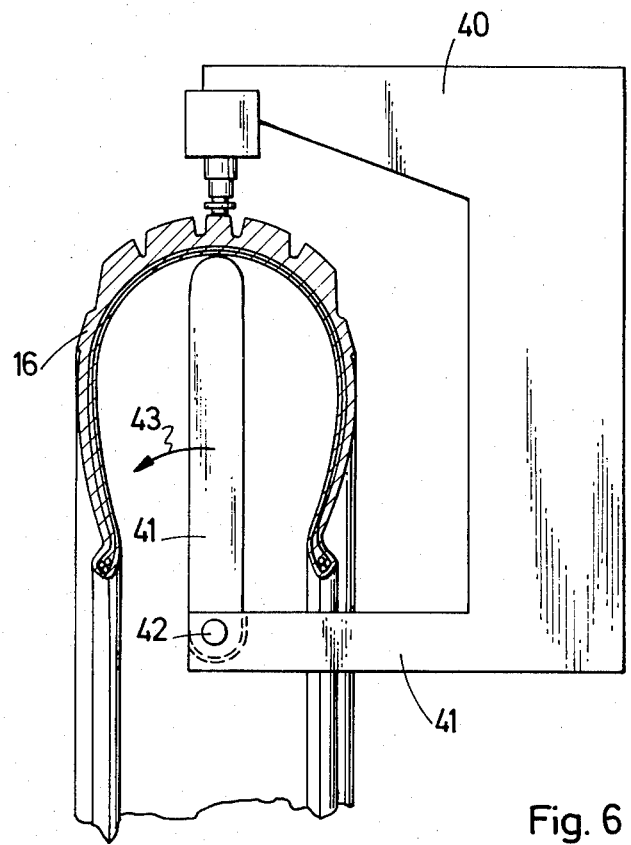
FIG. 6 is a diagrammatic front view of another particular embodiment of the apparatus according to the invention.

In FIG. 6 is shown another essential embodiment of the apparatus according to the invention which is mostly suitable to test casings from automobile tires.

The feature of this embodiment lies in that the space between table 17 and impression body 2 where that material to be tested is to be arranged, can be reached as well as possible, substantially independently from the size and shape of the test sample. In the present case the test sample 16 can thus be the finished product, more precisely an outer tire.

When testing tires, it may be desirable to use a ball-shaped impression body 2 with a diameter lying between 0.5 and 10 mm, which acts on the tire outer side.

The constant impression depth may then vary between 1 to 10% of the casing thickness at the level of the tire tread.

In this embodiment, the impression body 2 is mounted on the free end from an arm 40 which forms a substantially rigid unit with a projecting support 41 on which table 17 is adjustably mounted underneath the impression body.

To let tires 16 be arranged inside the apparatus as shown in FIG. 6, said table is swingable away from a vertical position to a substantially horizontal position about a pivot pin 42 as shown by arrow 43.

Said apparatus may for instance be provided at the end of a production line and allows by a simple pressure test, to control very accurately and reliably whether the tires have been made with the suitable rubber formulation, the adherence between the steel wires and the rubber has no failure and the vulcanizing rate of the unit is sufficient.

The invention is in no way limited to the above embodiments and many changes can be brought therein without departing from the scope of the invention as defined by the appended claims.

It is for instance possible to automatize the mechanism for imparting said deformation by means of pressurized air, electromagnetically (double magnet) or mechanically (with a spring).

It is further possible to use strain gauges instead of a piezo-electric component, to measure that force being exerted on the test sample, mostly when relatively large deformations are generated.

Finally it may be of importance according to the invention, to arrange damping means such as a rubber block, between stop member 7 and guide 6, to prevent possible vibrations which might appear with the direct metal-to-metal contact.

We claim:

1. Method for determining static and dynamic material characteristics, more particularly the elasticity modulus E' and loss modulus E'', from a viscous-elastic material the relaxation modulus E(t) of which fulfills the equation $E(t) = A + Bt^{-\alpha}$ with E(t) being the relaxation modulus, A and B being constants, and t the time in seconds, as a function of the frequency the material is subjected to, in which to that material the above defined characteristics of which are to be measured, there is applied by means of a force F, a constant predetermined deformation by compression or pressing-in and said deformation is retained for at least 10 seconds and preferably at least 15 seconds, whereby the building-up of force from a moment zero which corresponds to that time where said force is applied, and the decrease after said constant deformation has been reached, is measured as a function of the time, and said material characteristics are determined on the basis of the following formulas:

$$E(t) = f[F_1(a), F_2(b), F(t)] \qquad (I)$$

with
a = impression depth;
b = size and shape of the impression body or section of test sample $$E(t) = A + Bt^{-\alpha} \qquad (II)$$

$$E^x(\omega) = E'(\omega) + jE''(\omega) \qquad (III)$$

with $\omega = 2\pi F$ wherein f is the frequency;

$$E'(\omega) = \frac{\alpha B \omega^\alpha}{2(1+\alpha)} \Gamma\left(1 - \frac{\alpha}{2}\right) \Gamma\left(\frac{\alpha}{2}\right) + A \qquad (IV)$$

$$E''(\omega) = \frac{\alpha B \omega^\alpha}{2\Gamma(1+\alpha)} \Gamma \frac{(1-\alpha)}{2} \Gamma \frac{(1+\alpha)}{2} \qquad (V)$$

wherein $\Gamma$ is the common gamma function and j is $\sqrt{-1}$.

2. Method as defined in claim 1, in which such a deformation is applied that the total change in the cross-section of the deformed material which lies substantially at right angle to the direction of the applied force F, is to be neglected.

3. Method as defined in claim 1, in which said force F is applied but to a portion from a determined side of the material, in such a way that the total deformation of said material is to be neglected.

4. Method as defined in claim 3, in which said force F is applied in the form of a substantially point-like pressure load.

5. Method as defined in claim 3, in which said deformation is applied by means of a ball-shaped impression body over a depth which is equal at the most to the radius of said body.

6. Method as defined in claim 5, in which use is made of a ball-shaped impression body with a diameter lying between 0.5 and 10 mm, preferably between 0.5 and 3 mm.

7. Method as defined in claim 1, in which said deformation is applied to the material in less than 0.5 seconds and preferably less than 0.1 second.

8. Method as defined in claim 1, in which use is made of a test material sample the thickness of which is at least equal to five times the maximum deformation depth.

9. Method as defined in claim 1, in which use is made of a test sample with such a size that the ratio of the shortest spacing from the sample edge to the impression body, to the body width is at least four.

10. Method as defined in claim 1, in which use is made of an automobile tire as test sample.

11. Method as defined in claim 1, in which said force F is determined as a function of the time by means of periodic measurings or recordings with a frequency which decreases after said constant deformation has been reached.

12. Method as defined in claim 11, in which the measurings are performed from the moment zero up to before reaching said constant deformation with a frequency in the range from 50 to 200 measurings per second.

13. Apparatus for determining static and dynamic material characteristics, more particularly the elasticity modulus E' and loss modulus E'', from a viscous-elastic material the relaxation modulus E(t) of which fulfills the equation $E(t) = A + Bt^{-\alpha}$ wit E(t) being the relaxation modulus, A and B being constants, and t the time in seconds, as a function of the frequency the material is subjected to, in which to that material the above defined characteristics of which are to be measured, there is applied by means of a force F, a constant predetermined deformation by compression or pressing-in and said deformation is retained for at least 10 seconds and preferably at least 15 seconds, whereby the building-up of force from a moment zero which corresponds to that time where said force is applied, and the decrease after said constant deformation has been reached, is measured as a function of the time, and said material characteristics are determined on the basis of the following formulas:

$$E(t) = f[F_1(a), F_2(b), F(t)] \qquad (I)$$

with
a = impression depth;
b = size and shape of the impression body or section of test sample $$E(t) = A + Bt^{-\alpha} \qquad (II)$$

$$E^x(\omega) = E'(\omega) + jE''(\omega) \qquad (III)$$

with $\omega = 2\pi F$ wherein f is the frequency;

$$E'(\omega) = \frac{\alpha B \omega^\alpha}{2(1+\alpha)} \Gamma\left(1 - \frac{\alpha}{2}\right) \Gamma\left(\frac{\alpha}{2}\right) + A \qquad (IV)$$

-continued $$E''(\omega) = \frac{\alpha B\omega^\alpha}{2\Gamma(1+\alpha)} \Gamma\frac{(1-\alpha)}{2} \Gamma\frac{(1+\alpha)}{2} \quad (V)$$

wherein $\Gamma$ is the common gamma function and j is $\sqrt{-1}$, said force F being applied by a pressure body which is made fast together with a piezoelectric force transducer which is isolated from temperature changes to a component which is movable over a constant determined distance, which force transducer measures the force exerted along the component movement direction on said pressure body as a function of the time, whereby detection means are provided to switch on said force transducer at that moment when said movable component is brought from a rest position to an impression position.

14. Apparatus for determining static and dynamic material characteristics, more particularly the elasticity modulus E' and loss modulus E'', from a viscous-elastic material the relaxation modulus E(t) of which fulfills the equation $E(t)=A+Bt^{-\alpha}$ with E(t) being the relaxation modulus, A and B being constants, and t the time in seconds, as a function of the frequency the material is subjected to, in which to that material the above defined characteristics of which are to be measured, there is applied by means of a force F, a constant predetermined deformation by compression or pressing-in and said deformation is retained for at least 10 seconds and preferably at least 15 seconds, whereby the building-up of force from a moment zero which corresponds to that time where said force is applied, and the decrease after said constant deformation has been reached, is measured as a function of the time, and said material characteristics are determined on the basis of the following formulas:

$$E(t)=f[F_1(a), F_2(b), F(t)] \quad (I)$$

with
a = impression depth;
b = size and shape of the impression body or section of test sample $$E(t)=A+Bt^{-\alpha} \quad (II)$$

$$E^x(\omega)=E'(\omega)+jE''(\omega) \quad (III)$$

with $\omega=2\pi F$ wherein f is the frequency;

$$E'(\omega) = \frac{\alpha B\omega^\alpha}{2(1+\alpha)} \Gamma\left(1-\frac{\alpha}{2}\right)\Gamma\left(\frac{\alpha}{2}\right) + A \quad (IV)$$

$$E''(\omega) = \frac{\alpha B\omega^\alpha}{2\Gamma(1+\alpha)} \Gamma\frac{(1-\alpha)}{2} \Gamma\frac{(1+\alpha)}{2} \quad (V)$$

wherein $\Gamma$ is the common gamma function and j is $\sqrt{-1}$, said force F being applied by a pressure body which is made fast together with a force transducer to a component which is movable over a constant determined distance, which force transducer measures the force exerted along the component movement direction on said pressure body as a function of the time, said component comprising a rod which is slidably mounted inside a fixed guide and is provided at that end thereof removed from the impression body, with a stop member which cooperates on the one hand with a resilient member provided between the guide and the stop member, and on the other hand with a cam which is rotatable about a rotation axis which lies substantially at right angle to the rod axis, with an eccentricity which corresponds substantially to half said constant determined movement distance of the rod and thus can bring said rod together with the impression body, from a rest position in the direction of a test sample to an impression position, whereby in said impression position the stop member is pressed by the cam against the guide in such a way that in said position, a rigid dynamic connection is obtained between the rod, the impression body and the apparatus frame, and whereby detection means are provided for switching on said force transducer at that moment when the rod is moved in the direction of the test sample towards said impression position.

15. Apparatus as defined in claim 14, in which said detection means comprise at least one photocell with an interrupter which is movable in front thereof and is fast relative to said cam.

16. Apparatus as defined in claim 14, in which said cam is provided with a ball bearing or small wheel arranged eccentrically, the eccentricity thereof corresponding substantially to half said constant movement distance of the rod.

17. Apparatus for determining static and dynamic material characteristics, more particularly the elasticity modulus E' and loss modulus E'', from a viscous-elastic material the relaxation modulus E(t) of which fulfills the equation $E(t)=A+Bt^{-\alpha}$ with E(t) being the relaxation modulus, A and B being constants, and t the time in seconds, as a function of the frequency the material is subjected to, in which to that material the above defined characteristics of which are to be measured, there is applied by means of a force F, a constant predetermined deformation by compression or pressing-in and said deformation is retained for at least 10 seconds and preferably at least 15 seconds, whereby the building-up of force from a moment zero which corresponds to that time where said force is applied, and the decrease after said constant deformation has been reached, is measured as a function of the time, and said material characteristics are determined on the basis of the following formulas:

$$E(t)=f[F_1(a), F_2(b), F(t)] \quad (I)$$

with
a = impression depth;
b = size and shape of the impression body or section of test sample $$E(t)=A+Bt^{-\alpha} \quad (II)$$

$$E^x(\omega)=E'(\omega)+jE''(\omega) \quad (III)$$

with $\omega=2\pi F$ wherein f is the frequency;

$$E'(\omega) = \frac{\alpha B\omega^\alpha}{2(1+\alpha)} \Gamma\left(1-\frac{\alpha}{2}\right)\Gamma\left(\frac{\alpha}{2}\right) + A \quad (IV)$$

$$E''(\omega) = \frac{\alpha B\omega^\alpha}{2\Gamma(1+\alpha)} \Gamma\frac{(1-\alpha)}{2} \Gamma\frac{(1+\alpha)}{2} \quad (V)$$

wherein $\Gamma$ is the common gamma function and j is $\sqrt{-1}$, said force F being applied by a pressure body which is made fast together with a force transducer to a component which is movable over a constant determined distance, which force transducer measures the force exerted along the component movement direction on said pressure body as a function of the time, whereby detection means are provided to switch on said force transducer at that moment where said movable component is brought from a rest position to an impression position, said detection means and force transducer being connected to an electronic circuit which converts the analog force signal measured by said force transducer into a digital form and couples the digital data to the memory of a computer, and said electronic circuit comprising means causing the converting of the analog force signal into digital form decreases in the frequency thereof after a determined time interval which is longer than the time required to bring said movable component to said impression position.

18. Apparatus for determining static and dynamic material characteristics, more particularly the elasticity modulus E' and loss modulus E'', from a viscous-elastic material the relaxation modulus E(t) of which fulfills the equation $E(t) = A + Bt^{-\alpha}$ with E(t) being the relaxation modulus, A and B being constants, and t the time in seconds, as a function of the frequency the material is subjected to, in which to that material the above defined characteristics of which are to be measured, there is applied by means of a force F, a constant predetermined deformation by compression or pressing-in and said deformation is retained for at least 10 seconds and preferably at least 15 seconds, whereby the building-up of force from a moment zero which corresponds to that time where said force is applied, and the decrease after said constant deformation has been reached, is measured as a function of the time, and said material characteristics are determined on the basis of the following formulas:

$$E(t) = f[F_1(a), F_2(b), F(t)] \quad \text{(I)}$$

with
a = impression depth;
b = size and shape of the impression body or section of test sample $$E(t) = A + Bt^{-\alpha} \quad \text{(II)}$$

$$E^x(\omega) = E'(\omega) + jE''(\omega) \quad \text{(III)}$$

with $\omega = 2\pi F$ wherein f is the frequency;

$$E'(\omega) = \frac{\alpha B \omega^\alpha}{2(1+\alpha)} \Gamma\left(1 - \frac{\alpha}{2}\right) \Gamma\left(\frac{\alpha}{2}\right) + A \quad \text{(IV)}$$

$$E''(\omega) = \frac{\alpha B \omega^\alpha}{2\Gamma(1+\alpha)} \Gamma\frac{(1-\alpha)}{2} \Gamma\frac{(1+\alpha)}{2} \quad \text{(V)}$$

wherein $\Gamma$ is the common gamma function and j is $\sqrt{-1}$, said force F being applied by a pressure body which is made fast together with a force transducer to a component which is movable over a constant determined distance, which force transducer measures the force exerted along the component movement direction on said pressure body as a function of the time, whereby detection means are provided to switch on said force transducer at that moment where said movable component is brought from a rest position to an impression position, and a height-adjustable table on which said test sample can be arranged against the impression body before pressing same into the sample, said pressure body being mounted at the free end of an arm which forms a substantially rigid unit with a projecting support on which said table is adjustably mounted underneath the pressure body.

19. Apparatus as defined in claim 18, in which the table is swingable outwards away from below said pressure body.

* * * * *